US008592552B2

(12) United States Patent
Alonso Martí et al.

(10) Patent No.: US 8,592,552 B2
(45) Date of Patent: Nov. 26, 2013

(54) ANTIVIRAL PEPTIDES FROM AFRICAN SWINE FEVER VIRUS WHICH PREVENT THE BINDING OF THE VIRUS TO DLC8

(75) Inventors: Covadonga Alonso Martí, Madrid (ES); Bruno Hernaez De La Plaza, Madrid (ES); José Angel Martinez Escribano, Madrid (ES)

(73) Assignees: Alternative Gene Expression, S.L. (Algenex), Madrid (ES); Instituto Nacional de Investigación y Tecnologia Agraria y Alimentaria, Madrid (ES)

( * ) Notice: Subject to any disclaimer, the term of this patent is extended or adjusted under 35 U.S.C. 154(b) by 318 days.

(21) Appl. No.: 12/739,415

(22) PCT Filed: Oct. 20, 2008

(86) PCT No.: PCT/EP2008/064155
§ 371 (c)(1),
(2), (4) Date: Apr. 23, 2010

(87) PCT Pub. No.: WO2009/053340
PCT Pub. Date: Apr. 30, 2009

(65) Prior Publication Data
US 2012/0289459 A1 Nov. 15, 2012

(30) Foreign Application Priority Data
Oct. 24, 2007 (ES) .................................. 200702792

(51) Int. Cl.
*C07K 14/00* (2006.01)
*A61K 38/00* (2006.01)

(52) U.S. Cl.
USPC .......................................... 530/324; 514/1.1

(58) Field of Classification Search
USPC .......................................... 530/324; 514/1.1
See application file for complete search history.

(56) References Cited

U.S. PATENT DOCUMENTS

| 7,396,531 B2 * | 7/2008 | Rath et al. ................... 424/186.1 |
| 2003/0162719 A1 * | 8/2003 | Rothbard et al. ............... 514/14 |
| 2008/0008721 A1 * | 1/2008 | Rath et al. ................... 424/186.1 |

FOREIGN PATENT DOCUMENTS

WO    WO 2008/129103    * 10/2008    ............. C07K 14/01

OTHER PUBLICATIONS

Alonso et al., 2001, African Swine Fever Virus Protein p54 Interacts with the Microtubular Motor Complex through Direct Binding to Light-Chain Dynein, Journal of Virology, 75(20): 9819-9827.*
Melikov et al., 2005, Arginine-rich cell penetrating peptides: from endosomal uptake to nuclear delivery, Cell Mol. Life Sci., 62: 2739-2749.*

Martinez-Moreno et al., 2003, Recognition of novel viral sequences that associate with the dynein light chain LC8 identified through a pepscan technique, FEBS Letters, 544: 262-267.*
Rodriguez-Crespo et al., 2001, Identification of novel cellular proteins that bind to the LC8 dynein light chain using a pepscan technique, FEBS Letters, 503: 135-141.*
Sun, Huaichang, et al.; "African swine fever virus gene j13L encodes a 35-27 kDa virion protein with variable numbers of amino acid repeats," Journal of General Virology, 1995, pp. 1117-1127, vol. 76.
López-Otín, C., et al; "Mapping and Sequence of the Gene Coding for Protein p72, the Major Capsid Protein of African Swine Fever Virus," Virology, 1990, pp. 477-484, vol. 175.
Bastos, A.D.S., et al.; "Genotyping field strains of African swine fever virus by partial p72 gene characterisation," Archives of Virology, 2003, pp. 693-706, vol. 148.
Covadonga, Alonso, et al.; "African Swine Fever Virus Protein p54 Interacts with the Microtubular Motor Complex through Direct Binding to Light-Chain Dynein," Journal of Virology, 2001, pp. 9819-9827, vol. 75.
International Search Report, Sep. 4, 2009.
Harrison, Alistair, et al.; "Chapter 7: The Molecular Anatomy of Dynein," Essays in Biochemisty, 2000. pp. 75-87, vol. 35; Abstract Only.
King, Stephen M.; "Organization and regulation of the dynein microtubule motor," Cell Biology International, 2003, pp. 213-215, vol. 27.
Enjuanes, L. et al.; "Titration of African Swine Fever (ASF) Virus," Journal of General Virology, 1976, pp. 471-477,vol. 32.
Afonso, Claudio L., et al.; "Characterization of P30, a Highly Antigenic Membrane and Secreted Protein of African Swine Fever Virus," Virology, 1992, pp. 368-373, vol. 189.
Melikov, K.; "Arginine-rich cell penetrating peptides: from endosomal uptake to nuclear delivery," Cellular and Molecular Life Sciences, 2005, pp. 2739-2749, vol. 62.
Tabares, E.; "Proteins Specified by African Swine Fever Virus., II. Analysis of Proteins Infected Cells and Antigenic Properties," Archives of Virology, 1980, pp. 119-132, vol. 66.
Cobbold, Christian, et al.; "The Major Structural Protein of African Swine Fever Virus, p73, Is Packaged into Large Structures, Indicative of Viral Capsid or Matrix Precusors, on the Endoplasmic Reticulum," Journal of Virology, 1998, pp. 5215-5223, vol. 72.
Nunes, J.F. Moura, et al.; "Ultrstructural Study of African Swine Fever Cirus Replication in Cultures of Swine Bone Marrow Cells," Archives of Virology, 1975, pp. 59-66, vol. 49.

(Continued)

*Primary Examiner* — Amber D Steele
(74) *Attorney, Agent, or Firm* — Tristan A. Fuierer; Andrew D. Gerschutz; Moore & Van Allen, PLLC

(57) ABSTRACT

New antiviral peptides interfering the binding of the virus to DLC8 are provided. A high number of pathogenic agents of viral origin use the dynein based intracellular transport machinery at some point of their infective cycle. The present invention consists of a new antiviral therapy consisting in the inhibition of viral infections produced by those virus that use the dynein system by mechanisms of interference mainly by preventing the interaction between the viral protein and the cellular DLC8 protein. The present invention discloses for the first time the blocking of the function of this interaction by peptides whose sequence comprises or consists of the totality or a partial sequence of the viral protein corresponding to the binding domain with DLC8.

5 Claims, 13 Drawing Sheets

(56) References Cited

OTHER PUBLICATIONS

Figure 3:
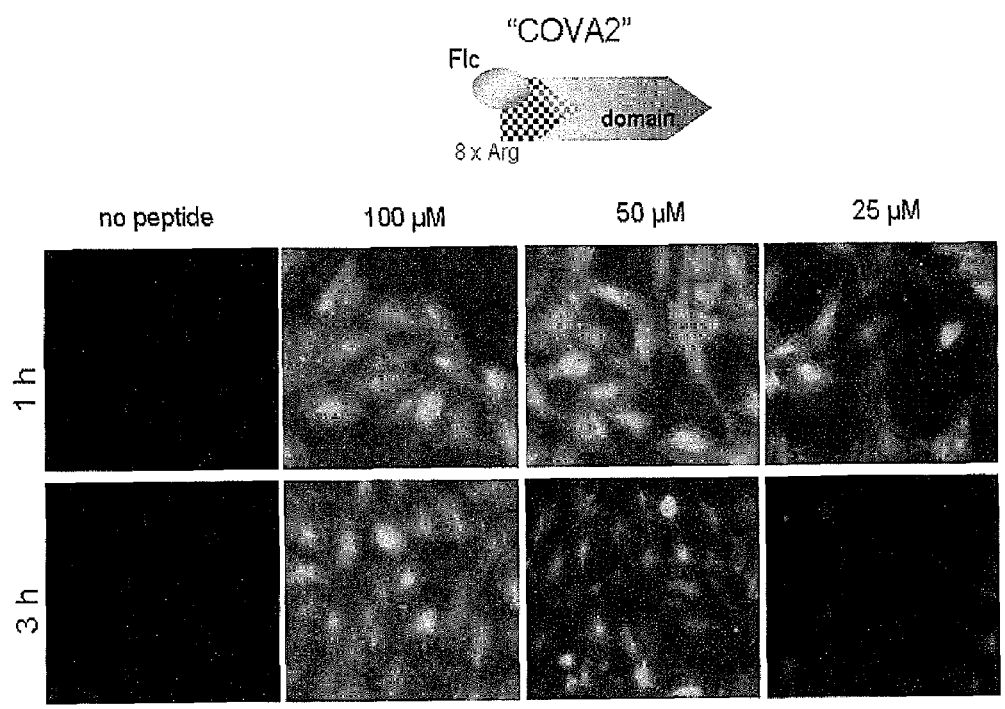

Martinez-Moreno, Monica, et al.; "Recognition of novel viral sequences that associate with the dynein light chain LC8 identified through a pepscan technique," FEBS Letters, 2003, pp. 262-267, vol. 544.

King, Donald P., et al.; "Development of a TaqMan, PCR assay with internal amplification control for the detection of African swine fever virus," Journal of Virological Methods, 2003, pp. 53-61, vol. 107.

Rodriguez-Crespo, Ignacio, et al.; "Identification of novel cellular proteins that bind to the LC8 dynein light chain using a pepscan technique," FEBS Letters, 2001, pp. 135-141, vol. 503.

Lo, Kevin W.-H, et al.; "The 8-kDa Dynein Light Chain Binds to its Targets via a Conserved (K/R)XTQT Motif," The Journal of Biological Chemistry, 2001, pp. 14059-14066, vol. 276.

Taylor, William Ramsay, "The Classification of Amino Acid Conservation," Journal of Theoretical Biology, 1986, pp. 205-218, vol. 119.

* cited by examiner

| | | | |
|---|---|---|---|
| BA71V | HPTEPYTTVTTQNTASQTMS | 163 | SEQ ID NO: 1 |
| E75 | HPTEPYTTVTTQNTASQTMS | 163 | SEQ ID NO: 1 |
| PRETORISUSKOP | HPAEPYTTVTTQNTASQTMS | 164 | SEQ ID NO: 1 |
| Lillie-148 | HPAEPYTAVTTQNTASQTMS | 164 | SEQ ID NO: 23 |
| Warthog | HPAEPYTTVTTQNTASQTMS | 173 | SEQ ID NO: 1 |
| Warmbath | YPAEPYTTVTTQNTASQTMS | 175 | SEQ ID NO: 24 |
| Tengani | HPAEPYTTVTTQNTASQTMS | 179 | SEQ ID NO: 1 |
| Portalegre90 | -PTEPYTTVTTQNTASQTMS | 163 | SEQ ID NO: 25 |
| mafra86 | -PTEPYTTVTTQNTASQTMS | 163 | SEQ ID NO: 25 |
| Almodovar99 | -PTEPYTTVTTQNTASQTMS | 163 | SEQ ID NO: 25 |
| Mkuzi | -PTEPYTTVTTQNTASQTMS | 163 | SEQ ID NO: 25 |
| Kenya1950 | -SAEPYTTATTQNTASQTMP | 155 | SEQ ID NO: 26 |
| MALAWI | ----------TDQLQTSQLQT | 131 | SEQ ID NO: 27 |

Figure 1

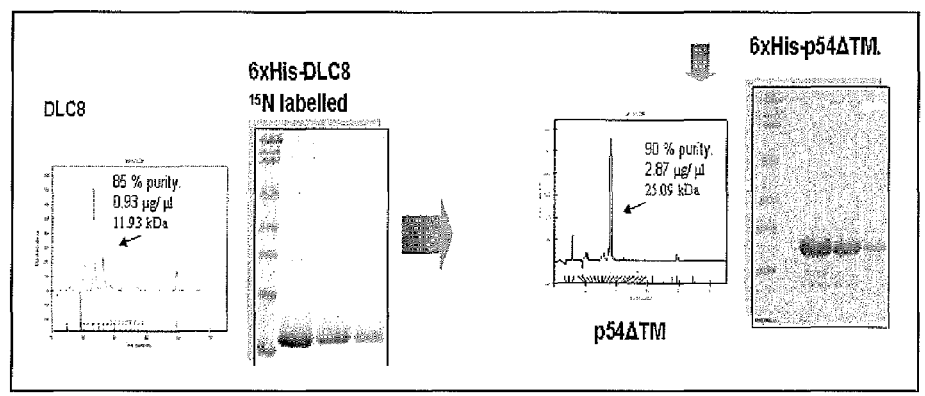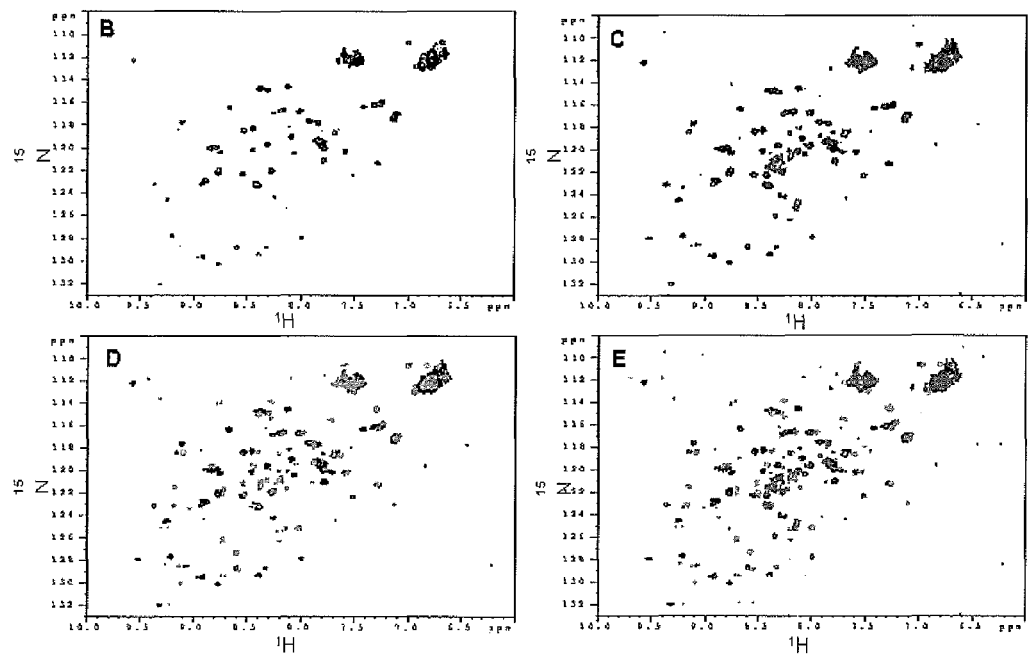
Figure 2

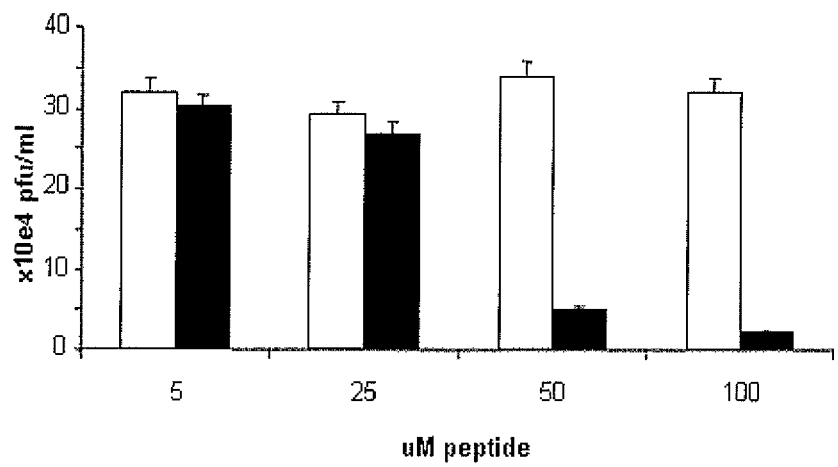
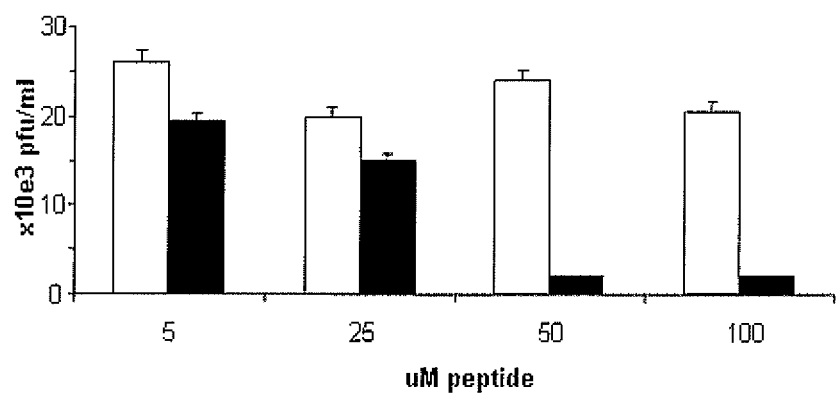
Figure 9

A
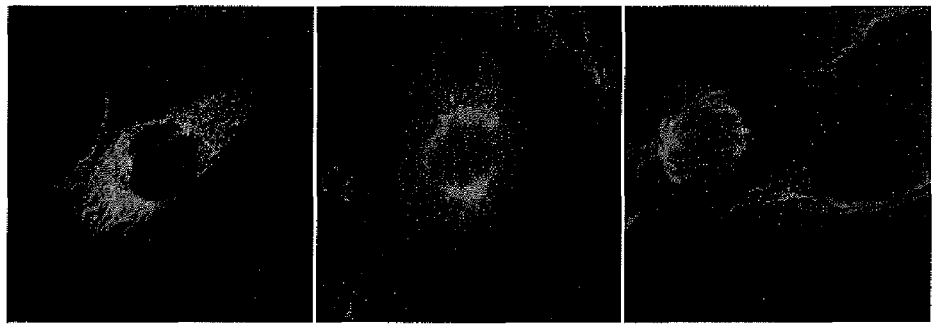
B
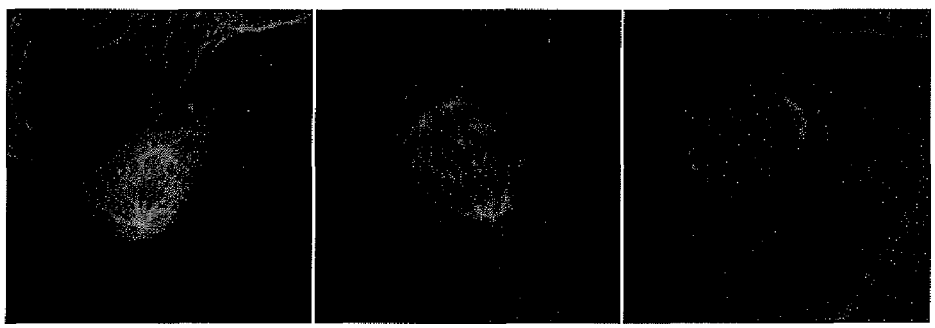
Figure 12

SEQUENCE LISTING

```
<160> NUMBER OF SEQ ID NOS: 29

<210> SEQ ID NO 1
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(3)
<223> OTHER INFORMATION: Xaa is Ala or Thr
<220> FEATURE:
<221> NAME/KEY: VARIANT
<222> LOCATION: (5)..(5)
<223> OTHER INFORMATION: Xaa is Pro or Ser
<220> FEATURE:
<221> NAME/KEY: VARIANT
<222> LOCATION: (6)..(6)
<223> OTHER INFORMATION: Xaa is Gly or Tyr
<220> FEATURE:
<221> NAME/KEY: VARIANT
<222> LOCATION: (7)..(7)
<223> OTHER INFORMATION: Xaa is Ser or Thr
<220> FEATURE:
<221> NAME/KEY: VARIANT
<222> LOCATION: (14)..(14)
<223> OTHER INFORMATION: Xaa is Thr or Ser
<220> FEATURE:
<221> NAME/KEY: VARIANT
<222> LOCATION: (16)..(16)
<223> OTHER INFORMATION: Xaa is Ser or Ala

<400> SEQUENCE: 1

His Pro Xaa Glu Xaa Xaa Xaa Thr Val Thr Thr Gln Asn Xaa Ala Xaa
1               5                   10                  15

Gln Thr Met Ser
            20

<210> SEQ ID NO 2
<211> LENGTH: 19
<212> TYPE: PRT
<213> ORGANISM: Artificial Sequence
<220> FEATURE:
<223> OTHER INFORMATION: Synthetic Construct

<400> SEQUENCE: 2

Pro Ala Glu Pro Tyr Thr Thr Val Thr Thr Gln Asn Thr Ala Ser Gln
1               5                   10                  15

Thr Met Ser

<210> SEQ ID NO 3
<211> LENGTH: 27
<212> TYPE: PRT
<213> ORGANISM: Artificial Sequence
<220> FEATURE:
<223> OTHER INFORMATION: Synthetic Construct

<400> SEQUENCE: 3
```

Arg Arg Arg Arg Arg Arg Arg Pro Ala Glu Pro Tyr Thr Thr Val
1               5                   10                  15

Thr Thr Gln Asn Thr Ala Ser Gln Thr Met Ser
            20                  25

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct

<400> SEQUENCE: 4

Ser Leu Val Ser Ser Asp Glu Ser Ser Ser Gly Ser Ser His Ser Ser
1               5                   10                  15

Gly Glu His Ser
            20

<210> SEQ ID NO 5
<211> LENGTH: 28
<212> TYPE: PRT
<213> ORGANISM: Artificial Sequence
<220> FEATURE:
<223> OTHER INFORMATION: Synthetic Construct

<400> SEQUENCE: 5

Arg Arg Arg Arg Arg Arg Arg Ser Leu Val Ser Ser Asp Glu Ser
1               5                   10                  15

Ser Ser Gly Ser Ser His Ser Ser Gly Glu His Ser
            20                  25

<210> SEQ ID NO 6
<211> LENGTH: 28
<212> TYPE: PRT
<213> ORGANISM: Artificial Sequence
<220> FEATURE:
<223> OTHER INFORMATION: Synthetic Construct

<400> SEQUENCE: 6

Arg Arg Arg Arg Arg Arg Arg Arg His Pro Ala Glu Pro Gly Ser Thr
1               5                   10                  15

Val Thr Thr Gln Asn Thr Ala Ser Gln Thr Met Ser
            20                  25

<210> SEQ ID NO 7
<211> LENGTH: 28
<212> TYPE: PRT
<213> ORGANISM: Artificial Sequence
<220> FEATURE:
<223> OTHER INFORMATION: Synthetic Construct

<400> SEQUENCE: 7

Arg Arg Arg Arg Arg Arg Arg Arg His Pro Ala Glu Pro Gly Ser Thr
1               5                   10                  15

Val Thr Thr Gln Asn Thr Ala Ser Gln Thr Met Ser
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic Construct

<400> SEQUENCE: 8

-continued

Arg Arg Arg Arg Arg Arg Arg Arg His Pro Thr Glu Ser Gly Ser Thr
1               5                   10                  15

Val Thr Thr Gln Asn Ser Ala Ala Gln Thr Met Ser
            20                  25

<210> SEQ ID NO 9
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: Xaa can be any naturally occurring amino acid

<400> SEQUENCE: 9

Xaa Xaa Xaa Xaa
1

<210> SEQ ID NO 10
<211> LENGTH: 25
<212> TYPE: DNA
<213> ORGANISM: Artificial Sequence
<220> FEATURE:
<223> OTHER INFORMATION: Synthetic Construct

<400> SEQUENCE: 10
ctgctcatgg tatcaatctt atcga                                          25

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
gataccacaa gatcagccgt                                                20

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12
ccacgggagg aataccaacc cagtg                                          25

<210> SEQ ID NO 13
<211> LENGTH: 14
<212> TYPE: PRT
<213> ORGANISM: African swine fever virus
<220> FEATURE:
<221> NAME/KEY: SITE
<222> LOCATION: (1)..(14)
<223> OTHER INFORMATION: p54 partial sequence responsible for binding to
      DLC8

<400> SEQUENCE: 13

Tyr Thr Thr Thr Val Thr Thr Gln Asn Thr Ala Ser Gln Thr
1               5                   10

<210> SEQ ID NO 14
<211> LENGTH: 5
<212> TYPE: PRT
<213> ORGANISM: Artificial Sequence

```
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa is Thr or Ser
<220> FEATURE:
<221> NAME/KEY: VARIANT
<222> LOCATION: (3)..(3)
<223> OTHER INFORMATION: Xaa is Ser or Ala

<400> SEQUENCE: 14

Xaa Ala Xaa Gln Thr
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: Variant
<222> LOCATION: (1)..(1)
<223> OTHER INFORMATION: Xaa is Lys or Arg
<220> FEATURE:
<221> NAME/KEY: Variant
<222> LOCATION: (2)..(2)
<223> OTHER INFORMATION: Xaa is any amino acid

<400> SEQUENCE: 15

Xaa Xaa Thr Thr
1

<210> SEQ ID NO 16
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: Variant
<222> LOCATION: (2)..(2)
<223> OTHER INFORMATION: Xaa is Ile or Val

<400> SEQUENCE: 16

Gly Xaa Gln Val Asp
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic construct

<400> SEQUENCE: 17

Tyr Ala Ser Gln Thr
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic construct

<400> SEQUENCE: 18

Tyr Ser Thr Gln Thr
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: Synthetic construct

<400> SEQUENCE: 19

Lys Ser Thr Gln Thr
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic construct

<400> SEQUENCE: 20

Lys Gln Thr Gln Thr
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic construct

<400> SEQUENCE: 21

Arg Val Met Gln Leu
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: Variant
<222> LOCATION: (1)..(1)
<223> OTHER INFORMATION: Xaa is Lys or Arg
<220> FEATURE:
<221> NAME/KEY: Variant
<222> LOCATION: (2)..(2)
<223> OTHER INFORMATION: Xaa is any amino acid

<400> SEQUENCE: 22

Xaa Xaa Thr Gln Thr
1               5

<210> SEQ ID NO 23
<211> LENGTH: 20
<212> TYPE: PRT
<213> ORGANISM: Artificial Sequence
<220> FEATURE:
<223> OTHER INFORMATION: Synthetic Construct

<400> SEQUENCE: 23

His Pro Ala Glu Pro Tyr Thr Ala Val Thr Thr Gln Asn Thr Ala Ser
1               5                   10                  15

Gln Thr Met Ser
            20

<210> SEQ ID NO 24
<211> LENGTH: 20
<212> TYPE: PRT
```

```
<213> ORGANISM: Artificial Sequence
<220> FEATURE:
<223> OTHER INFORMATION: Synthetic Construct

<400> SEQUENCE: 24

Tyr Pro Ala Glu Pro Tyr Thr Thr Val Thr Thr Gln Asn Thr Ala Ser
1               5                   10                  15

Gln Thr Met Ser
            20

<210> SEQ ID NO 25
<211> LENGTH: 19
<212> TYPE: PRT
<213> ORGANISM: Artificial Sequence
<220> FEATURE:
<223> OTHER INFORMATION: Synthetic Construct

<400> SEQUENCE: 25

Pro Thr Glu Pro Tyr Thr Thr Val Thr Thr Gln Asn Thr Ala Ser Gln
1               5                   10                  15

Thr Met Ser

<210> SEQ ID NO 26
<211> LENGTH: 19
<212> TYPE: PRT
<213> ORGANISM: Artificial Sequence
<220> FEATURE:
<223> OTHER INFORMATION: Synthetic Construct

<400> SEQUENCE: 26

Ser Ala Glu Leu Tyr Thr Thr Ala Thr Thr Gln Asn Thr Ala Ser Gln
1               5                   10                  15

Thr Met Pro

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Thr Asp Gln Leu Gln Thr Ser Gln Leu Gln Thr
1               5                   10

<210> SEQ ID NO 28
<211> LENGTH: 20
<212> TYPE: PRT
<213> ORGANISM: Artificial Sequence
<220> FEATURE:
<223> OTHER INFORMATION: Synthetic Construct

<400> SEQUENCE: 28

His Pro Ala Glu Pro Gly Ser Thr Val Thr Thr Gln Asn Thr Ala Ser
1               5                   10                  15

Gln Thr Met Ser
            20
```

```
<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29

Arg Arg Arg Arg Arg Arg Arg Arg
1               5
```

ANTIVIRAL PEPTIDES FROM AFRICAN SWINE FEVER VIRUS WHICH PREVENT THE BINDING OF THE VIRUS TO DLC8

FIELD OF THE INVENTION

This invention relates to the technical field of development of new antiviral compounds and their use in the prevention or treatment of virus infections in animals or human beings.

BACKGROUND OF THE INVENTION

Viruses are intracellular parasites which require the integrity of certain cell functions so that their replicative cycle within the cells can be successfully performed. Dynein has demonstrated having a relevant role in different steps of virus infection in different viral models such as rabies virus, the human Herpes simplex virus, type I or human immunodeficiency virus. Dynein is a microtubular motor protein, which intervenes in the intracellular transport linked to microtubules and the endosomal pathway and is modulator of different routes of translation of intracellular signals, among other functions. Viruses use dynein for their internalization and intracellular transport, for the formation of the viral factory where the new virions are going to be produced and for the regulation of the cellular signalling necessary in the coordination of these and other processes.

In particular, the protein p54 of the African swine fever virus (ASFV), interacts with a cell protein which is part of the microtubular motor complex called dynein and its function is essentially related to intracellular transport [1]. This interaction was found using the double hybrid system in yeast (an heterologous system), searching for interactor proteins in a swine macrophages cDNA library for possible interaction proteins of the viral p54 protein. The sequence coding for p54 (E183L gene) is included in the complete sequence of the BA71V isolate, deposited in the NCBI database with accession number UI8466. The clones obtained and identified as positive, were sequenced to discover that they contained the complete coding sequence of the light chain dynein of 8 kilodaltons (kDa), called DLC8, LC8, DLC1, DNLC1 or PIN (inhibitor protein of the neuronal nitric oxide synthetase). The sequence coding for DLC8 in Sus scrofa has been deposited in the NCBI database with number AF436777. These results were corroborated using another type of techniques including affinity chromatography, immunoprecipitation and colocalization of both components by confocal microscopy. Those results only confirmed the interaction between p54 protein of ASFV and DLC8.

DLC8 is a protein with a highly conserved nucleotide amino acid sequence between evolutionary distant species (from nematodes to man)[2, 3]. Cytoplasmic dyneins are a family of molecular motors which drive different loads throughout the microtubules. They are in charge of the transport of vesicles, endosomes and organelles from the exterior of the cell to the interior, to the nuclear or perinuclear zone. They are large multiprotein complexes, constituted by one to three heavy chains with a globular head and ATPase activity, which are responsible for generating the necessary energy to produce movement. Bound to these heavy chains are a variable number of intermediate chains and light chains. The latter are responsible for directly interacting with the load to transport. To date, seven families of light chains have been described, among which we can find DLC8. DLC8 is disposed as a dimer in viva, which permits the existence of two identical places of binding of different sequences among both monomers.

With respect to the cellular protein, two types of preferential binding sites with which they interact have been discovered for DLC8 [12, 13]. One of the motifs (Lys/Arg)XThrThr (with X being any amino acid) SEQ ID NO: 15 binds DLC8 with a series of molecules such as the intermediate chain of the dynein, the proapoptotic molecule Bim, Kid1 and Swallow transcription factors and some viral proteins of diverse origin. This binding site is located between the two dimers of the DLC8 molecule. The second motif is: Gly(Ile/Val)GlnValAsp SEQ ID NO: 16 which binds DLC8 to the neuronal nitric oxide synthetase (nNOS) or with the neuronal scaffolding protein, as described so far.

To identify the amino acid residues required for the binding of the viral protein to dynein, several truncated fragments of the p54 protein were expressed and tested in the yeast system to determine that the binding zone to DLC8 is located at the carboxy-terminal end of the p54 protein in 13 amino acids comprised between Tyr149 and Thr161 (TyrThrThrThrValThrThrGlnAsnThrAlaSerGlnThr) SEQ ID NO: 13 [1].

Several viruses use light chain dynein (DLC8) in different stages of their infective cycle inside the host cell. By a technique called pep-scan, peptides mimicking the linear sequences of different proteins of viral origin were synthesized, blotted on to filter paper and probed with DLC8 to determine which linear sequences were suitable for that interaction [10]. The linear sequences that appear below would be theoretically suitable for DLC8 binding. These frequently contain Gln (Q) residues, with often a T residue (Thr) contiguous in the sequence:

The TyrAlaSerGlnThr SEQ ID NO: 17 motif of the p54 protein of the African swine fever virus The TyrSerThrGlnThr SEQ ID NO: 18 motif of the binding glycoprotein of respiratory syncytial virus The LysSerThrGlnThr SEQ ID NO: 19 motif of the P protein of the rabies virus and of the Mokola virus, of the helicase of the human herpes simplex virus, of the adenovirus protease, or of the A. moorei entomopoxvirus.

The LysGlnThrGlnThr SEQ ID NO: 20 motif of the E4 protein of the human papillovirus or of the vaccinia virus polymerase.

The LysGlnThrGlnThr SEQ ID NO: 20 motif of gene U19 of the human herpes virus

The ArgValMetGlnLeu SEQ ID NO: 21 motif of the protein of the capsid of human Coxsackievirus, etc.

Even though some linear viral protein sequences have been found to be theoretically capable to bind DLC8, this does not preclude that all these sequences should be suitable for the interaction in the protein native form or as the molecule is integrated in the motor complex in vivo. Also, it is not demonstrated that those viral sequences are exposed somehow in the viral particle nor their putative binding sites to be able to bind DLC8 in fact, and/or if these viral proteins are synthesized in cellular compartments accessible to dynein during infection such as the cytosol (not endoplasmic reticulum or other secluded organelles and structures). Moreover, none of these linear sequences have been demonstrated to date to be able to block the binding of a given protein to DLC8 by any means, and finally, nothing guarantees that blocking this site would result in infection inhibition. In fact, there are two putative binding sites per DLC8 molecule as above described and there are a number of other light and intermediate chains that could be used alternatively by any given virus. In summary, none of these findings demonstrate that blocking this site would disrupt the interaction nor hamper virus infection and nothing guarantees that above mentioned sequences might be useful as antiviral compounds.

Moreover, for any peptide to be candidate to be used as antiviral, it should reach by some means the intracellular environment adequately and null or very low toxicity in living cells must also be assured. The fact that amino acid sequences may be identified as involved in the binding between viral proteins and DLC8, when those sequences stay on primary (linear) structure does not preclude, that those linear sequences will inhibit viral protein and DLC8 interaction and, accordingly, the peptides comprising those amino acid sequences may serve as antiviral compounds. Both interaction surfaces should be analyzed (for example by their nuclear magnetic resonance spectra) to design a peptide sequence suitable to block the protein-protein interaction. The reason for that lays on the fact that linear amino acid sequences, when folded in higher complexity structure in the cell, as a way of example, bound to a macromolecular complex called the microtubular motor complex, may hind the aminoacid residues involved in the binding with either DLC8 or the viral protein and, therefore, those secondary structure folded peptides would not show any anti-viral activity. Also, a defined sequence that in vitro or in an heterologous system as yeast would be involved in binding might not be exposed in the context of the viral particle and/or might be synthesized in a secluded organelle or structure, making it inaccessible to the cellular protein in the infection in mammalian cells. In all this cases, a peptide theoretically able to block interaction would not show any antiviral activity. An additional reason is that linear peptides when dissolved in the cell cytosol have a tendency to form aggregates which, on turn, would hid again the amino acids responsible of the binding either to DLC8 or to viral proteins. Those aggregated peptides would neither show anti-viral properties. Another important aspect in the design of novel anti-virus peptides relates to their toxicity in non-infected cells. A commercial anti-viral substance should prevent and/or inhibit viral infection but, preferably, without affecting cell viability and cell proliferation of non-infected cells. Last but not least, the invention has found that the amino acids surrounding the motifs involved in DLC8-viral proteins binding area, and particularly their hydrophobicity, they do play an important role in the binding inhibition capabilities of those peptides, to be considered as true anti-viral compounds. Antiviral peptides to achieve an effective inhibition of binding of viral proteins to DLC8 must be fully dissolved into the cell cytosol and, accordingly, the hydrophobicity and proline content of the amino acids neighbouring the binding motifs is crucial.

For all these reasons, it is necessary to generate antiviral strategies to block infection of said viruses by interference with the use that the viruses make of the cell dynein, i.e. either blocking its function or the binding sites which permit the different proteins of viral origin to use the dynein adequately. However, although some overlapping partial amino acid sequences, present in those virus, are repeated as binding motifs to DLC8, as KSTQT SEQ ID NO: 22 or GIQVD SEQ ID NO: 16, it is also important to inspect the neighbouring residues to assess if the interaction virus-DLC8 will effectively take place. Specific changes on those amino acids were assessed for their abilities to abolish interaction with DLC8.

We have demonstrated using a viral model (African swine fever virus, ASFV), that interfering of the system DLC8-Dynein, entails the blocking of the infection which provides the principal test for a new antiviral strategy which constitutes the object of the present invention.

We have compared the interaction domains of some of the proteins involved in the interaction and its flanking sequences and this information has been used to design peptides which act as the principal antagonists of the interaction of the pair of proteins which interact but that, at the same time, are tagged to reach the intracellular environment adequately and fulfil with all the requirements an antiviral compound must meet, mainly, as previously stated: specific inhibition of viral proteins—DLC8 binding in determined conditions, accessibility and solubility in the cell cytosol, no formation of aggregates and not interference on cell viability and proliferative capacity (no cell toxicity).

In conclusion, the present invention discloses for first time the use as anti-viral compounds of peptides, that were designed based in the sequence (total or partial) by which a virus binds dynein DLC8, as a necessary step for infection success, and those peptides are shown to be efficient inhibiting the viral infection in susceptible cells and to have a demonstrable antiviral effect. The inhibition of virus-DCL8 interaction is reflected in an inhibition of the viral cytopathic effect and a drastic reduction in the number of infected cells. Also, the antiviral effect of this compounds was measured quantitatively to compare their relative efficacy with quantitative PCR in terms of reduction in the copies of viral genomes per cell (which reflects the reduction in the viral replication in ng/µl found in the cell), and also it was measured the consequently significant reduction in virus production and in the synthesis of viral proteins. The invention is exemplified by peptides produced based in the p54 sequence of various ASFV isolates which prevent the infection to progress, being the basis for an antiviral therapy.

LEGENDS OF THE FIGURES

FIG. 1. Antiviral peptide design. Based on sequence analysis comparison of the viral ASFV protein p54 present in different viral isolates from diverse origins, we designed a set of peptides (Table 1) including the conserved motif and selecting the most favourable flanking sequences among those actually present in the viral protein with variations between different viral isolates.

FIG. 2. NMR dynamics of interaction and disruption by an active peptide. A. Obtention and purification of 15-N labelled DLC8 and p54 for NMR analysis. 1H-15N HSQC spectra of 15N-labeled DLC8 at different titration points: B, Free DLC8; C, free DLC8 (black spectrum) and with 2 eq of unlabeled p54 (grey spectrum); D, free DLC8 (black spectrum) and with 5 eq of peptide PS19 (SEQ ID NO: 2) and 2 eq of unlabeled p54 (grey spectrum); E, free DLC8 (black spectrum) with 5 eq of peptide PS19 and 2 eq of unlabeled p54 (grey spectrum) and with 2 eq of unlabeled p54 (grey spectrum).

FIG. 3. Demonstration of the internalization of peptides into cells. Fluorescein labeled peptide COVA2 (SEQ ID NO: 7) distribution in Vero cells incubated for 1 and 3 hours with different concentration of peptide constructions linked to an arginine-rich molecular transporter (COVA2). FITC-labelled peptide (COVA2) is internalized in 100% of the cells at a concentration of 100 µM peptide.

Figure 4:
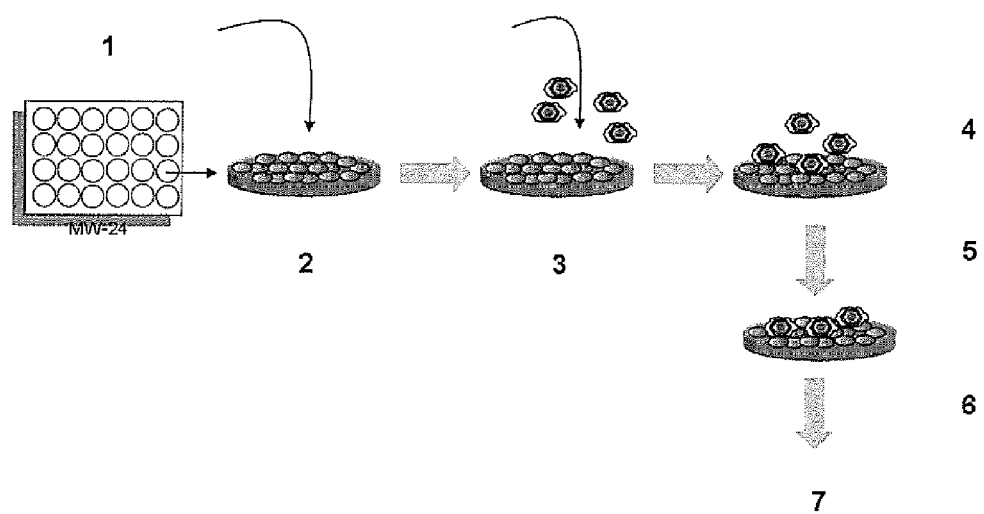

FIG. 4. Scheme of viral infection of cells and inhibition of said infection by the action of the peptides COVA1 (SEQ ID NO: 6) of the invention. 1.—Vero cells cultured at a density of $9 \times 10^4/cm^2$ the previous night in 5% DMEM. 2.—300 µl of solutions are added with different peptides in the range 0 to 100 µM in DMEM SC during 1 h at 37° C. for internalization of the peptides. 3.—Infection with 1 pf/cell of BA71V. 4.—Absorption of 2 h at 37° C. 5.—Elimination of the residual virus with 2 washes with 11 ml of DMEM SC. 6.—Course of the infection from 6 to 18 h post-infection in DMEM+peptides. 7.—Detection of infected cells.

Figure 5:
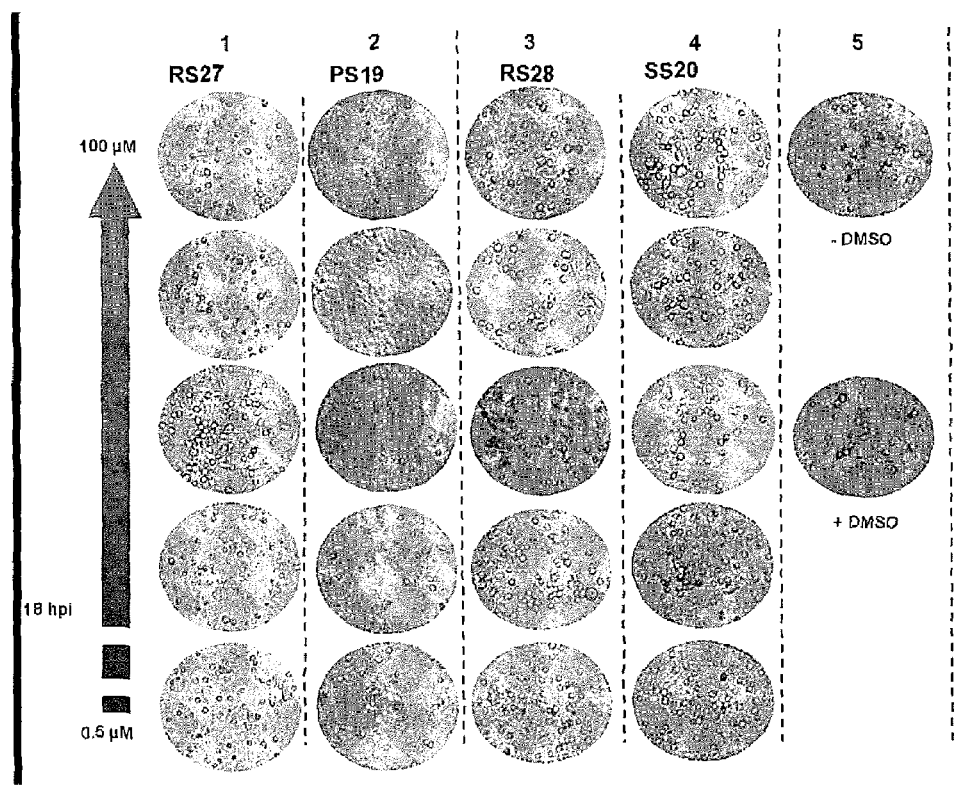

FIG. 5. Comparison of antiviral activity of antiviral and control peptides by cytopathic effect. Display by conventional microscopy (100× magnification) of the inhibition of the cytopathic effect of ASFV in the presence of rising concentrations of antiviral peptides (RS27—SEQ ID NO: 3— and PS19—SEQ ID NO: 2—) in columns 1 and 2, controls (RS28—SEQ ID NO: 5— and SS20—SEQ ID NO: 4—) in the columns 3 and 4 and in the absence of peptides in column 5.

Figure 6:
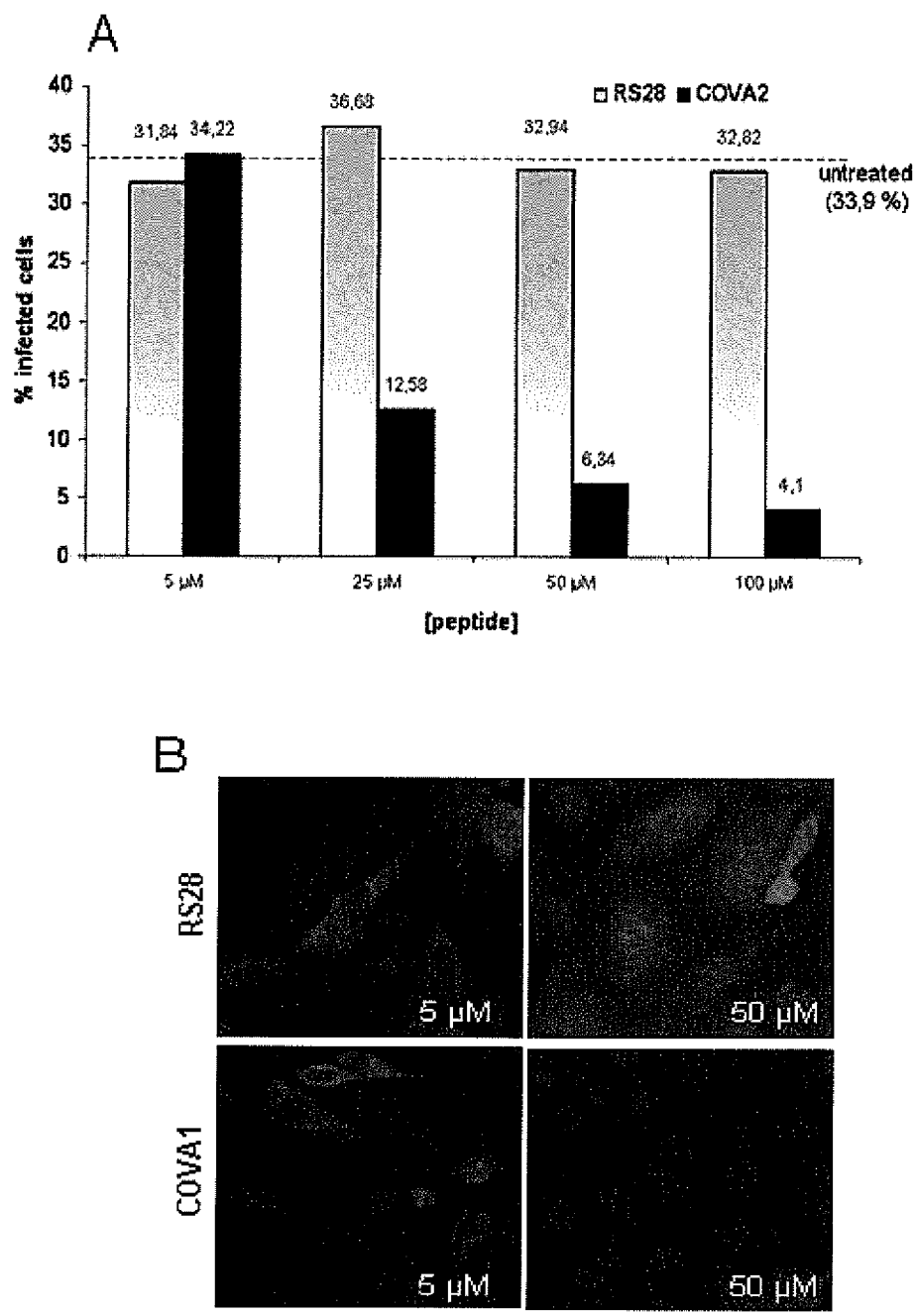

FIG. 6. Antiviral peptide treatment and infected cell number by immunofluorescence. FIG. 6A shows the percentages of infected cells at 6 hpi incubated with increasing concentrations of inhibitor (COVA2—SEQ ID NO: 7—) and control (RS28) peptides labeled with an antibody against ASFV p30. B shows a representative photograph of immunofluorescence assays of infected cells incubated with 5 µM and 50 µM of COVA2 and RS28 peptides.

Figure 7:
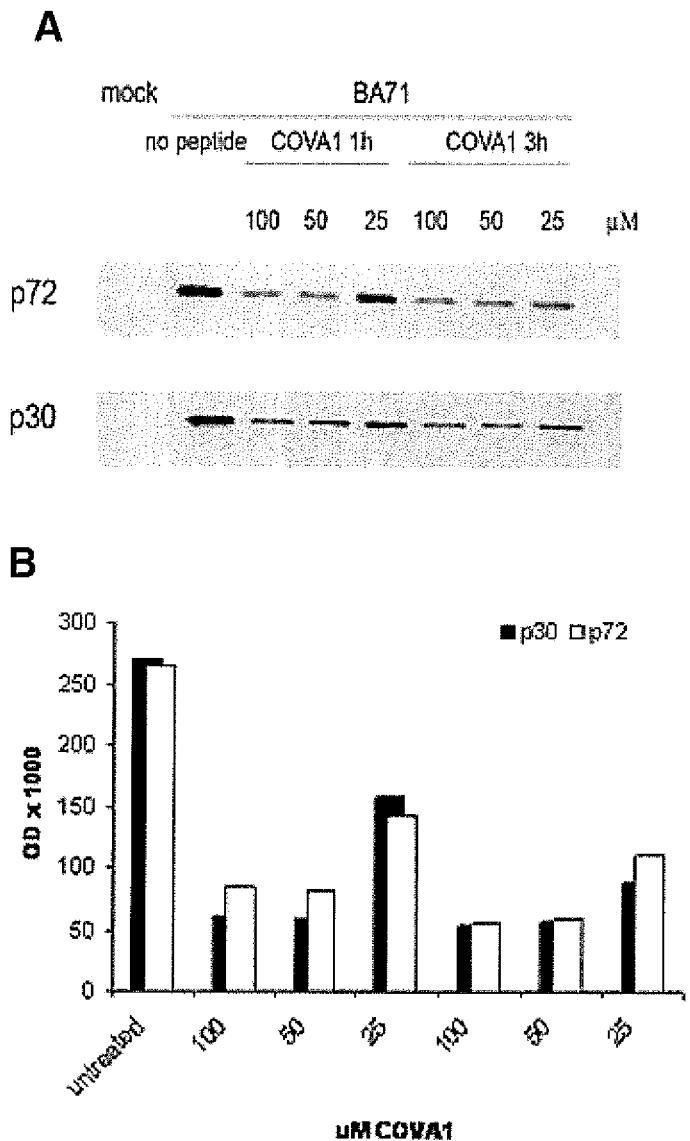

FIG. 7. Antiviral peptide treatment and viral protein synthesis. Analysis of early (p30) and late (p72) proteins synthesis with different concentrations of COVA1 (SEQ ID NO: 6) peptide for 1 and 3 hours. A, shows a representative gel of Western blot of p30 and p72 proteins and B shows the quantification of p30 and p72 proteins by densitometry.

Figure 8:
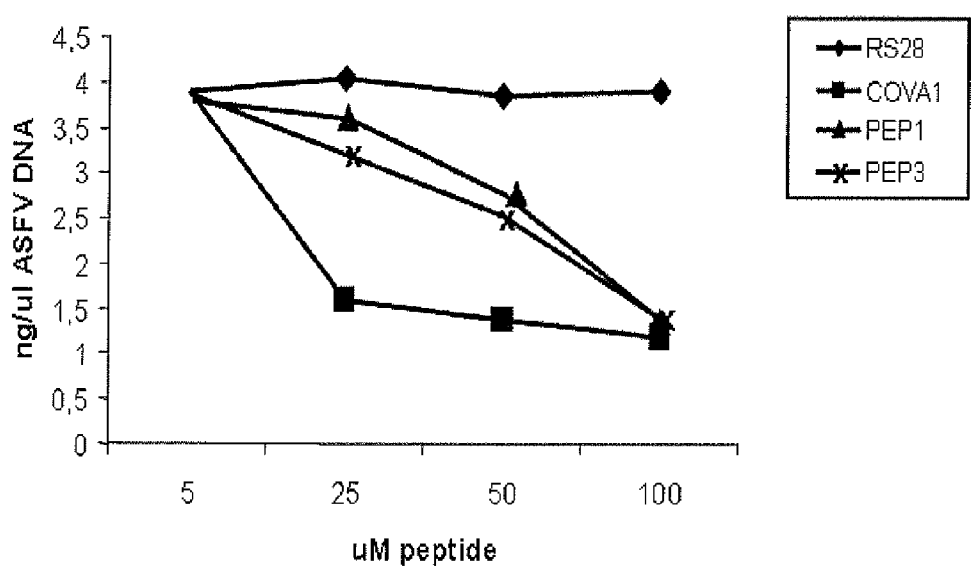

FIG. 8. Antiviral peptide treatment and quantitation of ASF viral DNA by quantitative PCR. Effect on ASFV DNA replication at 16 hpi after treatment with increasing concentrations of inhibitor peptide (COVA1, PEP1—SEQ ID NO: 9—and PEP3—SEQ ID NO: 8—) in comparison with control peptide RS28. Peptides containing other DLC8 binding sequences (PEP1 and PEP3) are also depicted in this figure indicating that COVA1 sequence is effective from lower peptide concentrations.

FIG. 9. Effect of antiviral peptide in virus production. Effect on intracellular (A) and extracellular (B) virus titers recovered after 36 hpi with increasing concentrations of inhibitor peptide COVA1 (black boxes) in comparison with control peptide RS28 (white boxes).

Figure 10:
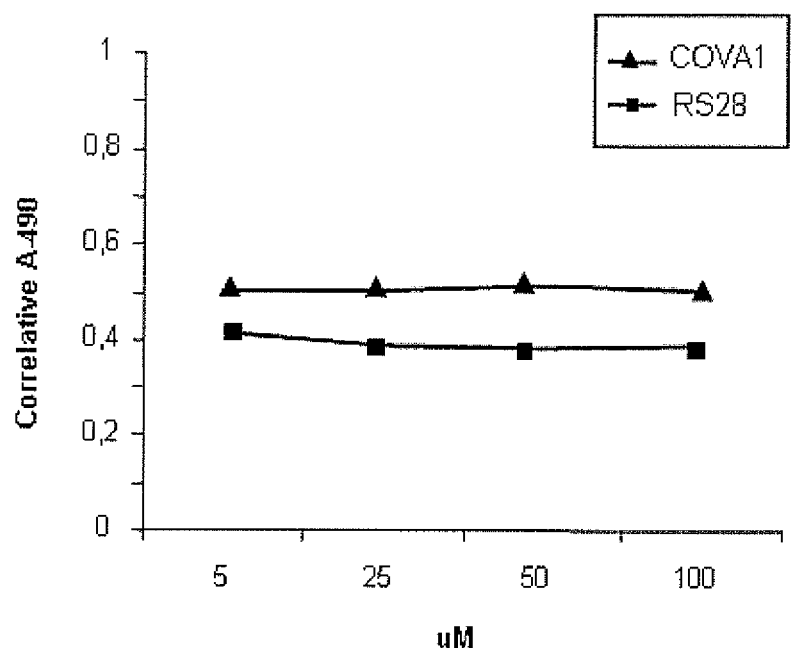

FIG. 10. Absence of cytotoxicity of the compounds. Proliferative index of Vero cells is not modified after 36 hours incubation of the antiviral (COVA1) and control peptide (RS28) at different concentrations.

Figure 11:
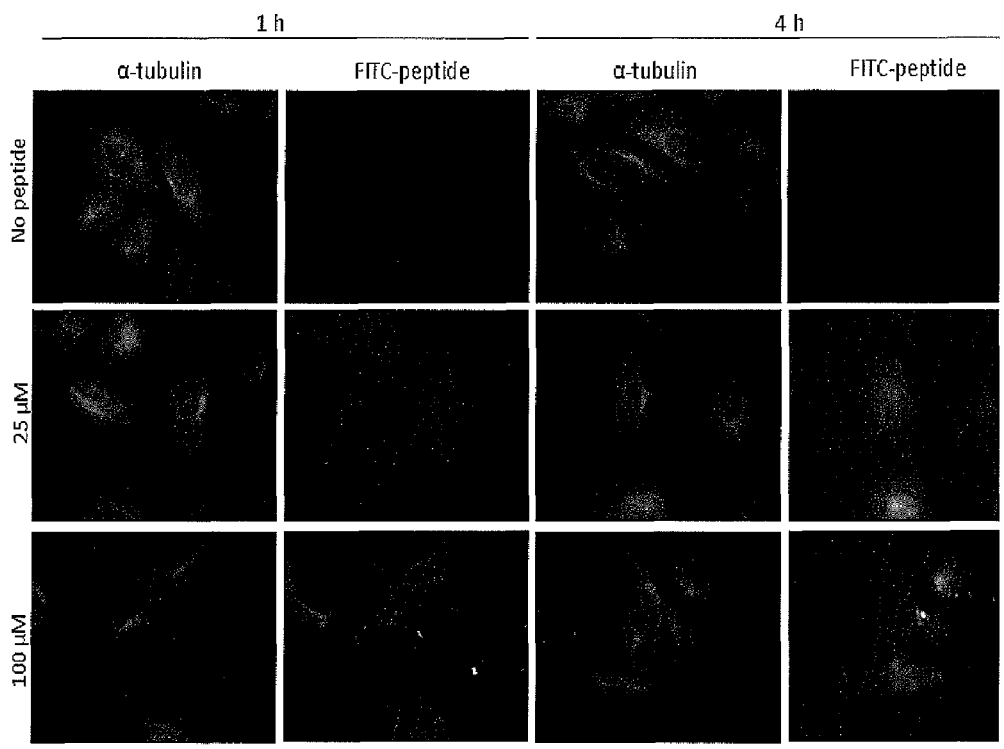

FIG. 11. Preservation of cell structures after peptide internalization A representative photograph of confocal microscopy of Vero cells treated with COVA2 peptide at different concentrations for 1 and 3 hours. The pictures show the conserved microtubule cytoskeleton architecture (tubulin) (left column) in non-treated cells and in cells treated with increasing concentrations of the peptide labelled with FITC (right column).

FIG. 12. Preservation of morphology and spindle formation during mitosis. A representative photograph of confocal microscopy of Vero cells treated with control (A) and inhibitor peptide COVA1 (B). Tubulin fibers forming the mitotic spindle during cell division in different stages both in control (A) and (B) peptide treated cells. The cells viability and proliferative capacity are not affected by peptide treatment.

Figure 13:
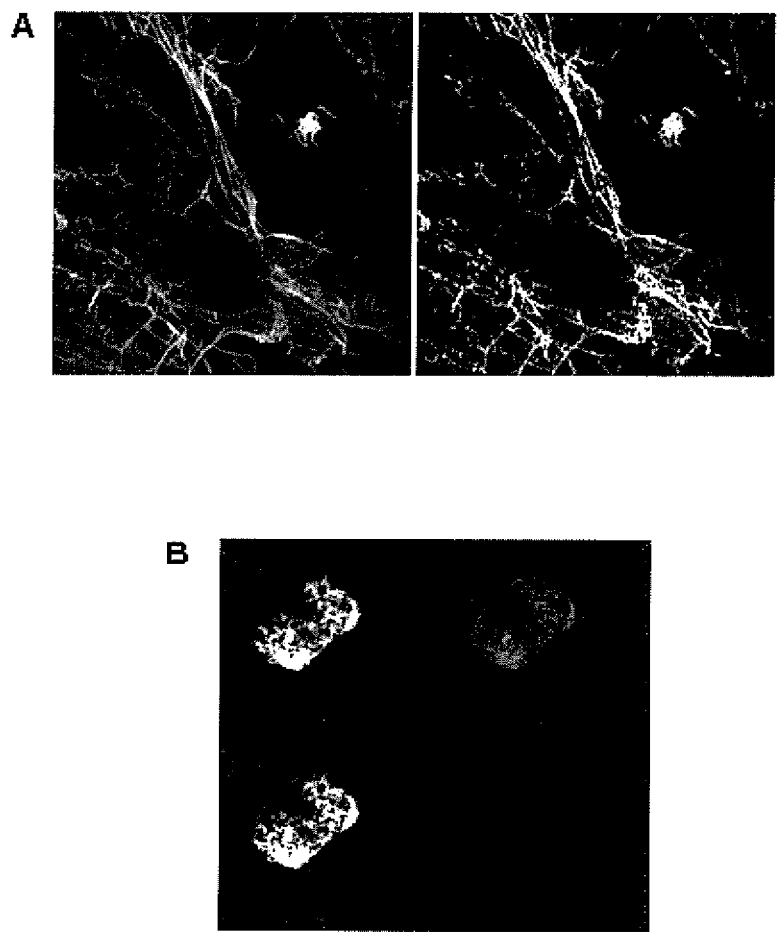

FIG. 13. Cellular distribution pattern of fluorescein labelled COVA2 peptide. Peptide binds one of the DLC8 cargo sites and the fluorescent peptide colocalizes with DLC8 precisely in its dynamic compartment such as cell projections (A), sites of cytoplasmic trafficking (A) and the cytoplasm of daughter cells after mitosis (B) where DLC8 functions repositioning organelles after cell division.

DESCRIPTION OF THE INVENTION

Based on a sequence analysis comparison of the viral ASFV protein p54 present in different viral isolates from diverse origins, we designed a set of peptides (Table 1) that included a consensus sequence conserved in most virus isolates and the most convenient flanking sequences among those that the protein present variations between the different viral isolates (FIG. 1). It was taken in consideration length, hydrophobicity and proline content. Proline can undergo cis/trans isomerization in solution and aggregates. Once we had selected the set of peptides, we synthesized those that were predicted to be soluble and stable by their aminoacid composition, and tagged them with a sequence to deliver them to the cells and then we proceed to test those peptides by the following approaches.

The nuclear magnetic resonance (NMR) technique allows an in depth analysis of the interaction surfaces between different proteins. In the present invention, it was analyzed the interaction between ASFV protein p54 and dynein light chain (DLC8) by NMR. This analysis have provided data which have made possible to know said interaction in detail, considering the tridimensional structure of both proteins and both surfaces of interaction allowing refining of the optimal peptide sequence to cover residues involved in interaction. NMR spectrum of DLC8 was obtained and it was evaluated how in presence of increasing concentrations of the viral p54, these spectrum was modified (chemical shift) indicating a high affinity interaction between both proteins. It was possible to determine the active center of the protein constituted by the residues of DLC8 that dissapeared from the spectrum because they are involved in the interaction. These residues are the following: Trp54, Lys9, Ser88, Asn61, Asn23, Asn33, Gly59, Ser86, Arg60, Glu15, and Tyr75. Then we were able to select the peptides which could bind and cover the residues involved in the surface of interaction and then it was tested which were able to prevent any further binding of the viral protein p54 at any concentration by blocking this high affinity interaction.

The present invention demonstrates that a correct interaction of the viral protein with cellular dynein is critical for the infection, that necessarily includes the intracellular transport of the virus from the membrane to the perinuclear zone (in an area corresponding to the microtubule organizing centre or MTOC, where the greatest accumulation of DLC8 occurs in healthy cells) and which, in the case of infection by ASFV, is where the viral factory is positioned and the viral proteins are synthesized to be assembled and give rise to new virions.

Recently, the studies performed using NMR mentioned above, have made it possible to demonstrate in our laboratory that it is possible to prevent the binding of p54 to DLC8, previously adding a peptide to DLC8 which includes the interaction sequence TyrThrThrThrValThrThrGlnAsnThrAlaSerGlnThr (SEQ ID NO: 13) existing in p54.

A preferred embodiment of the present invention consists of hindering the use of the dynein by the virus during the infection, by the use of a viral protein sequence, or part of it, to hinder the infection, in some cases by saturation of the binding sites of the cell protein by antiviral peptides antagonists of the viral protein-dynein bond. Within said peptides, the invention has proven in the treatment of cells of any origin with peptide sequences that they intervene in the action of viral proteins with the light chain dynein, for example those which contain the 14 amino acids: TyrThrThrThrValThrThrGlnAsnThrAlaSerGlnThr (SEQ ID NO: 13), including the changes of conservative amino acids in that sequence and in the analogues of sequence of different animal virus or functional analogues to this peptide. It was found that hydrophobicity of the flanking sequences to the critical motif (sequence of amino acids that maintain the interaction between p54-DLC8, Thr Ala Ser Gln Thr—SEQ ID NO: 14—) modified the ability of a peptide to bind DLC8. The design of peptide sequences have to consider that the peptide should bind to DLC8 in a specific site that is located in a hydrophobic canyon as shown by the tridimensional structure of the DLC8. Given the fact that from the theoretical sequences expected to bind DLC8, some of them bound and some other failed to bind DLC8 in vitro as it was explained above, present invention has gone further to refine the peptide sequence using NMR and a set of inhibitor peptides was selected. We demonstrated that p54-DLC8 interaction is a high affinity interaction as defined by their NMR interaction dynamics. Nevertheless, we were able to block this high affinity interaction adding some peptides showing for first time that p54-DLC8 interaction could be hindered interfering the bond with given peptide sequences (Table 1). The optimal peptide sequences selected were able to block the interaction while others were used as control peptides that did not modify interaction dynamics between p54 and DLC8 analyzed by NMR.

This methodological approximation of the present invention also includes any treatment of any origin with peptide sequences which comprise any of the previous sequences or with changes of conservative amino acids in said sequences. They include all the conservative transformations of those sequences and all the known mechanisms at present aimed at transporting these peptides to the interior of the cells, for example: Any of the peptides joined to sequences translocative to the interior of the cell (aminocaproic or aminohexinoic acid addition, etc); liposomes or any other vehicle which serves to internalize said peptides in the cell such as vectors, particularly viral vectors such as adenovirus or retrovirus, plasmids, etc., preferentially those vectors being linked to tag sequences. Treatment with peptides has the object of saturating the dynein binding motifs which use the transport linked to dynein preincubating them with the light dynein chain, the DLC8 protein, or any sequence of amino acids contained therein, or any peptide which contains the motifs (Lys/Arg) XThrGlnThr SEQ ID NO: 22 or Gly(Ile/Val)GlnValAsp, SEQ ID NO: 16 or sequences derived thereof with conservative changes of amino acids. Conservative changes are defined as those which do not change the load, the topology or the formation of the protein. Likewise, the invention comprises any of the previous peptides bound to other peptide sequences, peptide translocators, etc., or supplied together with liposomes and other vehicles to internalize the peptides in the cell and, in general, the transportation systems known at present for cells of any origin.

DETAILED DESCRIPTION OF THE INVENTION

Therefore, object of invention are antiviral composition of peptides selected from P54 sequence from different viral isolates, which are able to compete for the binding to DLC8 with viral proteins. Particularly those peptides must efficiently prevent the binding of the protein and the virus to DLC8 in vitro and in vivo and, accordingly, to inhibit viral infection. Among those peptides, it can be selected peptides pertaining to the sequences involved in viral protein-DLC8 interaction, either isolated from the viral protein sequence or from the DLC8 sequence itself. Any peptide derived thereof, particularly with conservative amino acid substitutions would also be included in present invention [14: Taylor, W. R.].

The peptides selected, apart for inhibiting viral-protein interaction with DLC8, must show no toxicity when incubated with cells to which antiviral protection is sought. Moreover, most of the peptides isolated which are involved in viral protein binding to DLC8, either isolated from the viral protein or from the light chain of dynein (DLC8) show a tendency to aggregate and to form dimers. When that takes place, their ability for binding is much lower and it can even disappear. That dimer formation and/or aggregation can be conveniently avoided by changing some amino acids in the sequences of those peptides considering hydrophobicity, total length and proline content. The invention has investigated those changes and it has selected a family of peptides which hamper virus binding to DLC8, by a high affinity competitive binding to DLC8, show no aggregation or formation of dimers and has low toxicity for the cell in which viral infection must be either prevented or treated.

Additionally, the peptides selected have a tail of Arg, in the number of 8 as a way of example, to facilitate those peptides to come inside the cells in which viral infection must be either prevented or treated.

The family of peptides selected (PS19, COVA1, COVA2, PEP1 and PEPS) they all derive from the portion of sequence pertaining to P54, responsible of the binding with DLC8. The family of peptides of the invention is represented by SEQ ID NO: 14 and comprises any other peptide derived thereof by conservative substitution in at least one of the amino acids of SEQ ID NO: 14. The subfamily of peptides represented by SEQ ID NO: 1 is particularly of interest due to their non-toxic effects on the cells.

The antiviral compositions of the invention comprising at least one peptide of the family represented either by SEQ ID NO:14 or SEQ ID NO: 1, may additionally comprise any other active compound and/or pharmaceutically acceptable excipient, carrier or diluent.

Among the viral infections that may be treated with the antiviral compositions of invention would be: ASFV, human papilloma virus, adenovirus, entomopoxvirus *A. moorei*, vaccinia virus, respiratory syncytial virus, human Coxsackievirus, rabies virus, human herpes simplex virus, Mokola virus or the AIDS virus.

Another object of present invention consists in a selection method of antiviral compounds and of evaluation of their efficacy characterized in that it involves:
  a) Preincubating or premixing a cell culture with a compound capable of binding to DLC8 either tagged with adequate intracellular delivery sequences or combined to known delivery methods such as liposomes, etc transfected with a vector expressing said peptide sequences
  b) Placing in contact the virus with the cell culture incubated or mixed previously in stage a)
  c) Detecting and quantifying the level of viral infection inside the cell after a time
  d) Comparing said level of viral infection with that reached in a cell culture infected with the virus, without preincubating or premixing with the compound capable of binding to DLC8

Another subject of present invention consists in a selection method of antiviral compounds and of evaluation of their efficacy characterized in that it involves:
  a) Preincubating or premixing a virus with a compound which comprises a sequence capable of binding to DLC8, a partial sequence thereof or an analogous sequence produced by conservative substitution of at least one amino acid of the sequence capable of binding to DLC8 or of a partial sequence thereof
  b) Placing in contact a cell culture with the virus incubated or mixed previously from stage a)
  c) Detecting and quantifying the level of viral infection inside the cell after a time
  d) Comparing said level of viral infection with that reached in a cell culture infected with the virus without preincubating or premixing with the compound of stage a)

Also, other object of present invention relates with the research of viral routes inside the cell, associated with the dynein transport system. A research method characterized by labelling a set of peptides capable of binding DLC8, is also covered in present invention which may be detected by, as a way of example, by direct fluorescence microscope. As labelling marker any of the available in cell research can be selected: fluorescein, rhodamine or other fluorescent and non-fluorescent markers such as biotin, haemaglutinin, c-myc, etc. . . . preferentially used as tags for detection with secondary antibodies, etc.

Finally, the invention also relates to a method for assessment of the inhibition of binding of ligands to DLC8 by measuring changes in light chain dynein (DLC8) spectra.

The following examples are preferred embodiments of executing the related inventions contained in present application and are given without scope limiting purposes, just to allow the man skilled in the art to reproduce those related inventions without undue effort.

EXAMPLE

Inhibition of the Infection by African swine Fever Virus (ASFV) by Peptides which Prevent Interaction Between p54 and the Cell Dynein Light Chain of 8 kDa (DLC8)

1.1. Materials 1.1.1 Cell Lines and Culture Media Used

Throughout this example the Vero cell line has been used as a model. The infections and internalization tests of peptides were developed in this established cell line, aneuploid and of indefinite growth in culture. It is derived from the adult African green monkey kidney (*Cercopithecus*) and it was obtained through the European Collection of Cell Cultures (ECACC), deposited with number 84113001. Their morphology is of fibroblast type and it was always used in a number of steps less than 20, keeping them frozen and aliquoted in liquid nitrogen until their use. This cell line was cultured using Eagle medium modified by Dulbecco (DMEM, Lonza), supplemented with 5% foetal bovine serum (BFS, Lonza) inactivated during 30 minutes at 56° C., 4 mM glutamine (Invitrogen), 200 IU/ml of penicillin and 100 mM streptomycin (Invitrogen). The culture conditions of the cells were 37° C. and an atmosphere of 5% $CO_2$. Routinely, these cells were subcultured 1:6 on two occasions a week, growing in Easy-T-Flasks culture flasks, 75 $cm^2$ coated with Nunclon® (Nunc).

The DMEM culture medium was supplemented in several forms depending on the particular test requirements. Thus, we refer to DMEM SC when it was used without antibiotics, glutamine or SBF. We refer to 2% DMEM when the percentage of SBF is added in this percentage maintaining the other additives in the concentrations mentioned in the previous paragraph.

For agarose plating, Dulbecco 2× (Gibco) medium was used.

1.1.2. Viral Isolates Used

The isolate of the African swine fever virus used in the inhibition tests of the infection was BA71V, adapted to grow in the Vero cell line [4]. The viral stock was conserved in aliquots of 100 µl at −80° C. in DMEM medium supplemented with 15% foetal bovine serum. At the time of their use, the aliquots necessary were quickly defrosted in a bath at 37° C. and kept in ice.

1.1.3. Fungible Material Used 1 ml capacity cryotubes (Nalgene) to conserve aliquoted the viral isolates and maintain a Vero cell line in liquid nitrogen.

Micropipettes (Gilson) with maximum capacities of 1000, 200 and 20 µl.

Micropipette tips (Arc) with filter and free from RNases, to avoid possible contaminations, of 1000, 200 and 20 µl capacity.

1.5 ml capacity tubes (Eppendorf) free from RNAses.

Multi-well cell culture plates of 4, 6, 12 and 24 wells (Nunc).

Coverslip of 12 mm diameter (Geyer Labs).

Conventional rectangular slides (Geyer Labs).

Nitrocellulose membrane for proteins, 9×7 cm (GE Healthcare).

Whatman paper, 9×7 cm.

1.1.4. Antibodies and Chromogens Used anti-p30 monoclonal antibody: developed in the laboratory of Dr. Jose Angel Martinez Escribano, specifically recognises and detects early protein p30 of the ASFV.

anti-DLC8 polyclonal antibody obtained in rabbits immunized with the DLC8 protein bound to 10 Histidine residues expressed in the heterologous system of *E. coli* and later purified. Generated in our laboratory.

anti-α tubulin monoclonal antibody (Sigma).

anti-p72 monoclonal antibody (anti-p73): marketed by Ingenasa, specifically recognises and detects structural late protein mainly p72 or p73 of the ASFV.

Mouse anti IgG antibody conjugated to the Alexa 594 fluorochrome (Molecular Probes).

Mouse anti IgG antibody conjugated to the Alexa 488 fluorochrome (Molecular Probes).

Mouse anti IgG antibody conjugated to HRP peroxidase (GE Healthcare).

Rabbit anti IgG antibody conjugated to HRP peroxidase (G Healthcare).

1.1.5. Other Reagents

Triton X-100 (Sigma).

Tween 20. (Sigma).

Phosphate buffer (PBS).

BSA, bovine serum albumin (Sigma).

ECL Chemoluminescence reagent (GE Healthcare).

RNAse-free water (Ambion).

RNAseZAP solution (Ambion) to eliminate RNAse activity from the working surfaces and materials.

ProLong, mounting reagent to conserve the fluorescence).

Hoechst 3332 (Sigma) as intercalating chromogenic agent of nucleic acids.

B-mercaptoethanol, SDS, Tris base (Sigma)

NP-40 (Fluka)

NaCl (Duchefa biochemicals).

Ultra pure low melting point agarose (Invitrogen).

1.1.6. Peptides Used

Different peptides were designed containing the DLC8 binding motif previously described in the ASFV p54 protein and another series of peptides of irrelevant sequence to use as negative controls (RS28 and SS20 peptides). All of them are described in Table no. 1. In some peptides, some modifications are included such as the following:

Addition of 8 arginine residues (R) at the N-terminal end, with the aim of increasing the internalization of the peptide in the cell [6] (RS27; RS28; COVA1; COVA2; PEP3; PEP1).

Conjugation to fluorescein at the N-terminal end for its directly display by fluorescence microscopy (COVA2; PEP3; PEP1).

Substitution of specific residues to facilitate the dissolution of the peptide and avoid its aggregation (COVA1, COVA2, PEP1 and PEP3)

Substitution of residues within the ThrAlaSerGlnThr SEQ ID NO: 14 motif for others which maintain the capacity of p54 of interacting with DLC8 (PEP3) [1].

All the designed peptides used throughout the present example were synthesized by Sigma-Genosys. The purification thereof was carried out by HPLC obtaining in all cases a degree of purity over 90%. Once synthesized and purified, the peptides were received in the laboratory as a lyophilizate.

TABLE NO. 1

List of peptides used in Example 1

| Peptide | Other name | Sequence (aa) | Character- istics | No. residues | Molecular weight |
|---------|------------|---------------|-------------------|--------------|------------------|
| PS19    | INTSTP1    | SEQ. ID NO: 2 | (1)               | 19           | 2028             |
| RS27    | INTSTP2    | SEQ. ID NO: 3 | (1, 4)            | 27           | 3277             |
| SS20    | INTCT1     | SEQ. ID NO: 4 | (5)               | 20           | 1949             |
| RS28    | INTCT2     | SEQ. ID NO: 5 | (4, 5)            | 28           | 3199             |
| COVA1   | DNBLK1     | SEQ. ID NO: 6 | (1, 3, 4)         | 28           | 3294             |
| COVA2   | DNBLK2     | SEQ. ID NO: 7 | (1, 2, 3, 4)      | 28           | 3653             |
| PEP3    | DNBLK3     | SEQ. ID NO: 8 | (1, 2, 3, 4, 6)   | 28           | 3652             |
| PEP1    | DNBLK4     | SEQ. ID NO: 9 | (1, 2, 3, 4)      | 28           | 3673             |

(1) contains binding sequence to DLC8 present in p54.
(2) conjugated to fluorescein
(3) contains changes with respect to the binding sequence to DLC8 present in p54 to avoid the aggregation and dimerization of the peptide.
(4) contains sequence of 8x arginines to facilitate their internalization in the cell
(5) negative control
(6) substitutions in the DLC8 binding motif present in p54 which do not modify the binding between both proteins.

1.2. Methods 1.2.1 Sequence Comparison Analysis

The sequence of p54 existing in different field and laboratory isolates of ASFvirus was plotted on a database and compared. Based on this sequence analysis comparison of the viral ASFV protein p54 present in different viral isolates from diverse origins, we designed a set of peptides (Table 1) that included a consensus sequence conserved in most virus isolates and the most convenient flanking sequences among those that the protein present variations between the different viral isolates (FIG. 1). For the peptide design, it was taken in consideration length, hydrophobicity and proline content. Proline can undergo cis/trans isomerization in solution and aggregates. The hydrophobic nature of the peptide may also be difficult to purify and facilitate precipitates. Once we had designed the set of peptides, we selected to be synthesized those that were predicted to be soluble and stable by their amino acid composition, and tagged them with a sequence to deliver them to the cells (an 8 arginine tail as detailed below) and then we proceed to test those peptides by the following approaches.

1.2.2. Nuclear Magnetic Resonance

Nuclear Magnetic resonance spectra were obtained after labeling with $N^{15}$ and purification of ASFV protein p54 and DLC8. The method used for this study is called chemical shift perturbation. First, both proteins were purified and spectra were compared with those reported by Lo et al, 1998 for DLC8 (FIG. 2).

1.2.3 Handling of the Peptides

According to their molecular weight (see Table no. 1), the peptides were resuspended in the volume of $H_2O$ with a corresponding degree of purity mQ and sterile, to obtain a stock solution at a concentration of 5 mM. Special attention was paid to avoid turbidity in the solution and tips were always used with a filter to avoid possible cross contaminations. 20 µl aliquots were made and they were conserved at −80° C. until the time of use. To use them their defrosting was slow, in ice.

The working solutions with the peptides were made from the stock solutions in DMEM SC medium in the 0-100 µM range of concentrations, always in sterile conditions and just before their addition to the cell culture to avoid their degradation.

1.2.4 Blocking of the p54-DLC8 Interaction by Peptides in Cell Culture $9 \times 10^4$ Vero cells were cultured in 24-well plates the night before the experiment. The next morning, the cells were washed in DMEM SC and the existing medium was replaced by 300 µl of the solutions containing the different peptides in different concentrations. The incubation of the cells with the peptides took place during 1 hour at 37° C. and 5% $CO_2$, after which the cells were infected with the ASFV. To infect the cells, the existing cell culture was removed and it was replaced to 2% 350 µl/well containing the corresponding quantity to obtain an infection multiplicity of 1 plaque forming unit (pfu) per cell. The infection was allowed to run until the desired time at 37° C. and 5% $CO_2$.

After the absorption period (2 h at 37° C.) the residual virus was eliminated by washing twice with DMEM SC and finally the cells were left in 300 µl of fresh DMEM SC containing the corresponding concentration of peptides. The infection was allowed to run at 37° C. for the desired time in each experiment, depending on the parameter of the infection to be analysed. This process is schematically represented in FIG. 4.

1.2.5 Detection of Cells Infected by ASFV by Indirect Immunofluorescence (IIF)

The detection of cells infected by ASFV in cells previously exposed to the different peptides was performed 6 hours post-infection. The IIF techniques used to detect those cells infected by ASFV by immunofluorescence were conventional. In summary, the cells were washed with 1 ml of PBS before being fixed with a 3.8% PBS-paraformaldehyde solution at ambient temperature during 10 minutes. The residual paraformadehyde was then eliminated by washing the cells 3 times with 1 ml of PBS. The permeabilization of cell membranes was performed using 0.2% PBS-Triton X-100 during 15 minutes at ambient temperature. After another 3 washes with PBS, the cells were incubated at 37° C. in blocking solution (3% PBS-BSA) during 45 minutes. As viral antigen to detect, the early protein of ASFV p30 [5] was chosen and its detection was carried out using the anti-p30 antibody diluted in PBS 1:200 during 1 hour at 37° C. The cells were washed 3 times with PBS and they were incubated for 30 minutes at ambient temperature with a solution with mouse anti-IgG antibody diluted 1:300 in PBS. The cells were washed in PBS and finally a marking of nuclei with Hoechst 3332 was incorporated. Finally, the coverslips containing the cells were mounted on slides using Prolong as mounting medium. The preparations were observed in a conventional fluorescence microscope (Leica) to count the number of positive cells for the viral antigen p30.

1.2.6. Analysis of the Synthesis of Viral Proteins by Western Blot During Infection by ASFV The viral proteins subject to analysis were early ASFV p30 protein expressed during the initial phases of the infection [5] and the p72 protein (on occasions also called p73) expressed during the late phase of the infection [7, 8]. The western blot was carried out on the cells, which were washed with 1 ml of cold PBS, before being collected in 50 µl of frozen RIPA protein extraction buffer (150 mM NaCl, 5 mM β-mercaptoethanol, 1% NP40, 1% SDS and 50 mM Tris-HCl pH=8). They were incubated at 4° C. with orbital stirring during 20 minutes to solubilize the proteins and then they were centrifuged at 12,000 rpm in a table centrifuge at 4° C. during 10 minutes. The precipitates were discarded and the supernatants were collected, which were stored at −70° C. until their analysis by western blot.

The samples were defrosted in ice and the quantity of protein in the different samples was quantified by the Bradford method. 20 μg of total denaturised protein at 100° C. during 5 minutes were separated by electrophoresis in 15% acrylamide:bis-acrylamide gels during 90 minutes at 100 V constant. The separated proteins were transferred to a nitrocellulose membrane during 90 minutes at 100 V constant in the presence of a transfer buffer (Tris-Glycine, 20% Methanol). The membrane was blocked in the presence of 50 ml of 5% skimmed PBS-milk powder at ambient temperature during a minimum of 1 hour with orbital stirring. Then, the membrane was hybridized with 10 ml of the anti-DLC8 polyclonal antibody diluted 1:50 in PBS during 1 hour at ambient temperature with stirring. After this time, the membrane was washed 3 times with 20 ml of 0.05% PBS-Tween at ambient temperature during 15 minutes on each occasion. Incubation with the secondary rabbit anti-IgG antibody conjugated to peroxidase and diluted 1:4000 in PBS lasted 1 h at ambient temperature with stirring. Having finalized this, the membranes were washed three times with 0.005% PBS-Tween during 15 minutes on each occasion. Finally, the detection by chemoluminescence using ECL was performed following the manufacturer's instructions in conventional manner.

As starting sample to analyse, total soluble protein extracts were used from Vero cells exposed or not to the different peptides and later infected or not with ASFV during 16 hours.

As primary antibodies the anti-p30 monoclonal antibody diluted 1:100 in PBS and the anti-p72 monoclonal antibody diluted 1:2000 in PBS were used in independent membranes. The membranes were incubated with both antibodies for 1 hour at room temperature with orbital stirring.

As secondary antibody, the mouse anti-IgG antibody conjugated to peroxidase were used in both cases.

Finally, the densitometry of the chemoluminescence reaction for quantifying and relativizing the quantity of protein existing in each band detected.

1.2.7. Detection and Quantitation of ASFV Genome

Detection and quantitation of ASFV genome was achieved by quantitative real time PCR using specific oligonucleotides (SEQ ID NO: 10 and SEQ ID NO: 11) and a TaqMan probe (SEQ ID NO: 12). DNA from infected or mock infected cells with BA71V 0.5 pfu/cel was extracted and purified with DNeasy blood and tissue kit (Qiagen) at 16 hpi. DNA concentration and purity was estimated by measuring the absorbance at 260 nm ($A_{260}$).

Amplification mixture was prepared on ice as follows:
3 μl template DNA (1 μg).
1 μl oligonucleotide OE3F 50 pmol.
1 μl oligonucleotide OE3R 50 pmol.
10 μl Quantimix Easy Probes Biotools 2×.
1 μl TaqMan™ probe SE2 5 pmol.
4 μl H$_2$O.

Amplification reaction was performed in a Rotor Gene 6000™ (Corvette Research), as indicated in following table:

| T$^a$ | time | n° cycles |
|---|---|---|
| 94 | 10 minutes | 1 |
| 94 | 15 seconds | 45 |
| 58 | 1 minute | |

Positive amplification controls (DNA purified from ASFV virions) and negative amplification controls (DNA from mock infected cells) were included in the assay and duplicates from every sample were analyzed.

1.2.7. Effect of Peptide Treatment on Virus Progeny Production During ASFV Infection.

9×10$^4$ Vero cells were seeded in 24-well plates the night before experiment. 1 h prior to infection cells were incubated in 300 μl DMEM containing different concentrations of COVA1 or RS28 peptides. Then, cells were infected or mock infected with 0.5 pfu/cell of ASFV BA71V strain. At 36 hpi, 100 μl of media was collected from wells and stored at −80° C. until analyzing extracellular virus progeny. Infected cells were also collected in 100 μl of fresh DMEM. Cells were frozen and thawed three times to enable solubilisation of intracellular virus progeny and then stored at −80° C. until use. Virus titres from intracellular or extracellular samples were analyzed by plaque assay. Briefly, Vero cells monolayers seeded in 6-well plates were inoculated with 50 μl of 10 fold serial dilutions of samples containing virus progeny. After a 90 minutes adsorption period, cells were washed twice in fresh DMEM 5% and 3 ml/well of overlay (low melting point agarose 2% and DMEM 2×, v:v) were added to cells. When overlay got solid, plates were incubated at 37° C. and 5% CO2 for 12 days. Then, cells were stained with 1% crystal violet in 5% formaldehyde to enable visualization of viral plaques. Virus titres were calculated as follows: pfu/ml=2×n° plaques×10$^{fold\ dilution}$ 1.2.9 Cytotoxicity Analysis. Cell Viability and Proliferation Assays.

To evaluate cell viability Vero cells seeded in 24 well plates were incubated in DMEM containing inhibitor peptide COVA1 or negative control RS28 at concentrations ranging from 0 to 100 μM. After incubation with peptides for 24 h, cells were harvested and the number of viable cells present in the cell suspensions was determined by Tripan blue (Sigma) dye exclusion assay. Briefly, 20 μl of PBS with Tripan Blue 0.08% were added to equal volume of cell suspension and mixed. After 2 minutes blue cells (dead cells) were counted using a hematocytometer and a conventional light microscope.

To evaluate cell proliferation 3×10$^4$ Vero cells seeded in 96 well plates were incubated in 50 μl DMEM containing inhibitor peptide COVA1 or negative control RS28 at concentrations ranging from 0 to 100 μM. After 36 h incubation, cell proliferation was determined using CellTiter 96 Aqueous™ (Promega) assay, following manufacturer's indications.

1.3. Results 1.3.1 Antiviral Peptides Design

The sequence of p54 existing in different field and laboratory isolates of ASFvirus was plotted on a database and compared. Based on this sequence analysis comparison of the viral ASFV protein p54 present in different viral isolates from diverse origins, we designed a set of peptides (Table 1) that included a consensus sequence conserved in most virus isolates and the most convenient flanking sequences among those that the protein present variations between the different viral isolates (FIG. 1). For the peptide design, it was taken in consideration length, hydrophobicity and praline content. Praline can undergo cis/trans isomerization in solution and aggregates. The hydrophobic nature of the peptide may also be difficult to purify and facilitate precipitates. Once we had designed the set of peptides, we selected to be synthesized those that were predicted to be soluble and stable by their aminoacid composition, and tagged them with a sequence to deliver them to the cells (an 8 arginine tail as detailed below) and then we proceed to test those peptides by the following approaches.

1.3.2. Analysis of Interaction Surfaces by Their Nuclear Magnetic Resonance Spectra Nuclear Magnetic resonance spectra were obtained after labeling with $N^{15}$ and purification of both proteins. The method used for this study is called chemical shift perturbation. This method analyzes the chemical changes observed in the target protein when it interacts with a ligand. First, both proteins were purified and spectra were compared with those reported by Lo et al, 1998 (13) for DLC8 (FIG. 2A). In presence of increasing concentrations of ASFV protein p54, the spectra of DLC8 changes, and signals involved in the binding motif disappeared progressively. At p54 concentrations of 0.1 eq, first disappearing signals corresponding to residues W54, K9, S88, N61, N23. When reaching 0.3 eq concentrations, disappearing signals correspond to residues N33, G59, N23, S86, R60, E15, y Y75 (FIG. 1A). The slow interchange of the interacting process observed between DLC8 and P54 indicated that binding between these proteins occurs at high affinity. Nevertheless, we have been able to interfere with this high affinity interaction when some peptides were added and no modifications of DLC8 spectra in any of the above mentioned residues from the active center of the protein was observed at any concentration of p54 (FIG. 2B) showing for first time that this interaction might be efficiently blocked with given peptide sequences (Table 1).

1.3.3. Internalization of the Peptides in Vero Cells

The bibliography describes that the addition of Arginine residues at the ends of a peptide significantly increases the penetration of them to the cell interior. With said purpose, we incorporated an intracellular delivery transporter composed of eight arginines. To check that the peptides designed are internalized with efficacy in the cell interior a fluorescein label was incorporated at the N-terminal end. Those peptides without the arginine intracellular delivery transporter were not able to enter the cell, while those incorporating the transporter tail were efficiently internalized and stained unambiguously almost 100% of the cells present in the culture, after 1 and 3 hour incubations with the peptide, in a microtubular continuous pattern (FIG. 3). The COVA2 peptide meets this set of characteristics, including the DLC8 binding motif previously described in p54, and it was used to directly view the internalization in Vero cells.

As can be observed in FIG. 3, the peptide was efficiently internalized, being possible for it to be detected easily by direct fluorescence microscope, even 6 h after its addition.

The optimum concentrations of COVA2 peptides were 50 and 100 μM, without significant differences between both concentrations. 25 μM of COVA2 could be detected, although with greater difficulty than in the higher concentrations, and however lower concentrations, i.e. below 5 μM could scarcely be detected by fluorescence microscopy.

1.3.4. Inhibition of the Infection by ASFV by Peptides that Block the p54-DLC8 Binding As detailed in the methods section of this example, infections were performed at 1 pfu/cell on a single-layer ASFV of Vero cells previously exposed to different peptides. The infection was left to run in the presence of the peptide and the following infection parameters were analysed to check the inhibitor effect of the peptides in question.

1.3.4.1. Effect of the Peptides on the Cytopathic Effect Characteristic of Viral Infection ASFV Infection produces a damage on the infected cells which is very characteristic and easily detectable as cytopathic effect by conventional microscopy. It starts early after the infection and finally leads to the progressive intracellular vacuolization, rounding of the cell contour and detachment of the surface to which the infected cell was adhered [9].

We evaluated the presence or absence of generalized cytopathic effect 18 hours post-infection in Vero cell cultures where the infection progressed in the presence of the different peptides. Using this method, it was possible to verify the inhibition of the cytopathic effect in those cell cultures incubated with peptides which contained in their sequence the DLC8 binding motif together with the arginine sequence to facilitate their entry into the cell interior. In contrast, those cells exposed to the control peptides or without the sequence of arginines developed a cytopathic effect similar to that observed in the cells where the infection was developed normally.

As depicted in FIG. 5, the degree of cytopathic effect observed was directly proportional to the concentration of peptide used. Thus, the concentrations of the PS19 peptide inhibited the cytopathic effect totally in the range of concentrations between 25 and 100 μM, but concentrations lower than 25 μM were not effective when inhibiting the cytopathic effect.

The following table summarizes the capacity of inhibition of the cytopathic effect for the different peptides tested and their corresponding concentrations.

TABLE NO. 2

| Peptide | Other names | DLC8 binding motif | 8 x Arginines | I.C.E. at 50 μM | I.C.E. at 100 μM |
|---------|-------------|--------------------|---------------|-----------------|------------------|
| PS19    | INTSTP1     | yes                | no            | no              | no               |
| RS27    | INTSTP2     | yes                | yes           | yes             | yes              |
| SS20    | INTCT1      | no                 | no            | no              | no               |
| RS28    | INTCT2      | no                 | yes           | no              | no               |
| COVA1   | DNBLK1      | yes                | yes           | yes             | yes              |
| COVA2   | DNBLK2      | yes                | yes           | yes             | yes              |
| PEP1    | DNBLK3      | yes                | yes           | yes             | yes              |
| PEP3    | DNBLK4      | yes                | yes           | yes             | yes              |

Furthermore, the peptide which contains the DLC8 binding motif with those modifications maintained the interaction ability of the peptide and demonstrated to be effective when inhibiting the cytopathic effect in the infection.

1.3.4.2. Effect of the Peptides on the Percentages of Cells Infected

The inhibitory effect of the peptides was analysed by counting the number of cells infected by the ASFV (positive for antigen p30). To do this, the cells were incubated in the presence of different inhibitor peptides and control peptides, previously to virus infection, as is detailed in the methods section of the present example.

As depicted in FIG. 6, incubation with the COVA2 peptide previous to the infection resulted in a drastic reduction in the percentage of infected cells, on comparing with the data obtained in cells incubated with the control peptide RS28. Furthermore, this reduction was dependent on the concentrations of COVA2 peptide used.

1.3.4.3. Effect of the Peptides on the Synthesis of Viral Proteins

The synthesis of early and late ASFV proteins was analysed by western blot using specific antibodies. Thus, it could be observed that both the synthesis of early (p30) and late (p72) viral proteins decreased dose-dependently when the infection by ASFV takes place in the presence of the COVA1 peptide. Furthermore, said reduction is dependent on the dose of COVA1 added to the cell culture (FIG. 7).

1.3.4.4. Effect of the Peptides Measured by Viral Genome Replication Counts Vero cells were pre-incubated with different peptide concentrations, as described before, and infected with BA71V ASFV isolate. Cells were harvested at 16 hpi and replication of ASFV genome was analysed by quantitative real time PCR using specific TaqMan probe and oligonucleotides [11]. As can be seen in FIG. 8, treatment with inhibitor peptide COVA1 strongly reduced dose-dependently the replication of ASFV genome. Similarly, pre-incubation with other blocking peptides (PEP1 and PEP3), which contained changes in DLC8 binding motive that not affect p54-DLC8 interaction, also resulted in a reduction of ASFV genome replication, although the treatment with COVA1 sequence is effective from lower peptide concentrations (25 µM). This reduction of viral DNA replication after peptide treatment is consequence of the inhibition of the infection by these peptides. Then, by this sensitive quantitative method it was possible to define within the peptides that can hinder p54-DLC8 bond and are interfering infection, that there are given sequences that can more effectively block the infection in vivo (FIG. 8).

1.3.4.5. Effect of Peptide Treatment on Virus Progeny Production During ASFV Infection.

$9 \times 10^4$ Vero cells growing in 24-well plates were treated with different concentrations of peptides COVA1 and RS28 for 1 h at 37° C., as described in materials and methods section. Cells were then BA71V infected or mock infected at 0.5 pfu/cell. At 36 hpi extracellular and intracellular virus progeny from infected cell cultures were analyzed by plaque assay. As shown in FIG. 9 a statistically significant decrease in the extra (FIG. 9B) and intracellular (FIG. 9A) virus titres calculated was observed when infection proceeds in the presence of 50 µM COVA1 or greater concentrations. Nevertheless, incubation with negative control peptide RS28 at different concentrations did not affect virus titres and resulting virus progeny values were similar to those from infected cells in absence of peptide.

1.3.5. Cytotoxicity Analysis. Effect of Peptide Treatment on Cell Viability and Proliferation To evaluate if any cytotoxicity or side-effects were linked to treatment of Vero cells with the peptides, cell proliferation and cell viability assays were performed. In these experiments, proliferation values of cells after treatment with different concentrations of COVA1 peptide did not decreased when compared to cells treated with the negative control peptide RS28 (FIG. 10). Proliferation values obtained with COVA1 were similar to those obtained in control cells in absence of peptides. Also, cell viability percentages were not modified after incubation with different peptides (inhibitor or control peptides), as judged from Tripan-blue exclusion assay. Cell viability percentages were around 90% in all cases. These results demonstrate that incubation with the peptides described in the present invention does not affect either the proliferation or viability of Vero cells.

1.3.5.1. Cellular Structure and DLC8 Functional Integrity

We tested if major cellular structures related to microtubular motor dynein were modified by peptide treatment. Together with peptide internalization, we analyzed the integrity of cytoskeletal components and we observed that microtubules were not modified in presence of the peptide COVA2 (FIG. 11). Also, light chain dynein distribution pattern on microtubules was conserved with a condensed area corresponding to the microtubular organizing center (MTOC) (FIG. 11). Dynein function is known to be important in mitosis, playing a role in the formation of the mitotic spindle and migration of chromosomes and we found that cell division was not altered (FIG. 12).

1.3.5.2. Cellular Distribution Pattern of Fluorescein Labeled COVA2 Peptide Fluorescein labeled peptide COVA2 showed a similar distribution as DLC8 stained using a polyclonal antibody against the whole DLC8 molecule. DLC8 interacts in the cytoplasm with selected cargoes mediating the transport of organelles, RNA and proteins to the minus end of the microtubules (towards the nucleus) and its function is essential for relocation of organelles such as Golgi after mitosis. Interestingly, COVA2 peptide colocalized precisely with the dynamic compartment of the DLC8 molecule. Fluorescent peptide was distributed mainly in cytoplasmic areas, cellular projections, filopodia and cellular contacts in resting cells. In cells undergoing mitosis, it remained in peripheral cytoplasmic areas until late phases of mitosis have occurred. Then, in cells undergoing karyokinesis and daughter cells, COVA2 staining increased and was very intense in all cytoplasmic areas in those cells undergoing redistribution of organelles after mitosis (FIG. 13) Colocalization percentages were higher in cells actively relocating cellular organelles after mitosis using the antibody staining the whole DLC8 molecule. Then, it was found to be a selective marker of a dynamic compartment linked to DLC8 mediated transport in cells.

These results demonstrate clearly that the viral infection (by the ASFV) can be inhibited using specially designed peptides based on the DLC8 binding motif existing in the viral p54 in different viral isolates which prevent the interaction between both proteins. This inhibition is reflected in an inhibition of the cytopathic effect, a drastic reduction in the number of infected cells, in the copies of viral genomes per cell (which reflects the reduction in the viral replication in ng/µl found in the cell), and the consequently significant reduction in virus production and in the synthesis of viral proteins.

In conclusion, the present invention uses for first time peptides which were designed based in the sequence by which a virus binds dynein DLC8, a necessary step for infection success, and those peptides are shown to be efficient inhibiting the viral infection in susceptible cells and to have a demonstrable antiviral effect.

BIBLIOGRAPHY

1. Alonso, C., et al., *African swine fever virus p54 protein interacts with the microtubular motor complex through direct binding to light-chain dynein*. J Virol, 2001. 75(20): p. 9819-27.
2. Harrison, A. and S. M. King, *The molecular anatomy of dynein*. Essays Biochem, 2000. 35: p. 75-87.
3. King, S. M., *Organization and regulation of the dynein microtubule motor*. Cell Biol Int, 2003. 27(3): p. 213-5.
4. Enjuanes, L., et al., *Titration of African swine fever (ASF) virus*. J Gen Virol, 1976. 32(3): p. 471-7.
5. Afonso, C. L., et al., *Characterization of p30, a highly antigenic membrane and secreted protein of African swine fever virus*. Virology, 1992. 189(1): p. 368-73.
6. Melikov, K. and L. V. Chernomordik, *Arginine-rich cell penetrating peptides: from endosomal uptake to nuclear delivery*. Cell Mol Life Sci, 2005. 62(23): p. 2739-49.
7. Tabares, E., et al., *Proteins specified by African swine fever virus. II. Analysis of proteins in infected cells and antigenic properties*. Arch Virol, 1980. 66(2): p. 119-32.
8. Cobbold, C. and T. Wileman, *The major structural protein of African swine fever virus, p73, is packaged into large structures, indicative of viral capsid or matrix precursors, on the endoplasmic reticulum*. J Viral, 1998. 72(6): p. 5215-23.
9. Nunes, J. F., J. D. Vigario, and A. M. Terrinha, *Ultrastructural study of African swine fever virus replication in cultures of swine bone marrow cells*. Arch Virol, 1975. 49(1): p. 59-66.

10. Martinez-Moreno, M. et al., *Recognition of novel viral sequences that associate with the light chain dynein LC8 identified through a pepscan technique.* FEBS Letters 2003. 544: 262-267.
11. King, D. P., et al., *Development of a TaqMan PCR assay with internal amplification control for the detection of African swine fever virus.* Viral Methods. 2003. 107: 53-61.
12. Rodríguez-Crespo, I., et al., *Identification of novel cellular proteins that bind to the LC8 dynein light chain using a pepscan technique.*, FEBS Lett. 503: 135-141 (2001).
13. Lo, K. W., et al., *The 8-kDa dynein light chain binds to its targets via a conserved (K/R)XTQT motif.* J. Biol. Chem. 276: 14059-14066 (2001).
14. Taylor, W. R., *The classification of amino acid conservation.* Journal of Theoretical Biology, 119: 205-218 (1986).

The invention claimed is:

1. An antiviral composition capable of binding to dynein light chain 8 (DLC8) comprising an isolated peptide consisting of an amino acid sequence of SEQ ID NO: 28, wherein the isolated peptide optionally is conjugated to a labeling marker selected from the group consisting of a fluorescent marker, a non-fluorescent marker, and an eight arginine tail having an amino acid sequence of SEQ ID NO: 29.

2. The antiviral composition according to claim 1, characterized in that the antiviral composition further contains means to increase the peptide internalization into the cell.

3. The antiviral composition according to claim 2, wherein the means to internalize the peptide into the cell consists of the eight arginine tail having the amino acid sequence of SEQ ID NO: 29.

4. The antiviral composition according to claim 1, which also comprises another active compound and/or any pharmaceutically acceptable vehicle, excipient, carrier or diluent.

5. An isolated peptide consisting of an amino acid sequence of SEQ ID NO: 28, wherein the isolated peptide is conjugated to a fluorescent marker or other labeling marker.

* * * * *